United States Patent
Kashiwagi et al.

(10) Patent No.: US 6,805,691 B2
(45) Date of Patent: Oct. 19, 2004

(54) HYGIENE PRODUCT

(75) Inventors: Masahiro Kashiwagi, Kagawa (JP);
Etsuko Tagami, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 38 days.

(21) Appl. No.: 10/334,998

(22) Filed: Dec. 31, 2002

(65) Prior Publication Data

US 2003/0130642 A1 Jul. 10, 2003

(30) Foreign Application Priority Data

Jan. 9, 2002 (JP) ........................................ 2002-002374

(51) Int. Cl.⁷ .............................................. A61F 13/15
(52) U.S. Cl. ............................ 604/385.02; 604/385.04; 604/385.13
(58) Field of Search ........................ 604/385.01, 385.02, 604/385.04, 385.05, 385.13

(56) References Cited

U.S. PATENT DOCUMENTS 4,701,178 A * 10/1987 Glaug et al. ................ 604/387
5,792,131 A * 8/1998 Mizutani ................ 604/385.02
6,074,376 A * 6/2000 Mills .......................... 604/390
6,168,582 B1 * 1/2001 Hasegawa .............. 604/385.02

* cited by examiner

Primary Examiner—John J. Calvert
Assistant Examiner—Jacqueline Stephens
(74) Attorney, Agent, or Firm—Darby & Darby

(57) ABSTRACT

Disclosed is a hygiene product including a sanitary napkin, a release sheet and a packaging sheet. Wing portions of the sanitary napkin are folded back against a body surface of a main body portion of the sanitary napkin, and pressure sensitive adhesive layers of the wing portions are covered with the release sheet. A stack of the packaging sheet, the sanitary napkin and the release sheet are so folded into the hygiene product that only the packaging sheet is exposed externally. A portion of the packaging sheet protruding rearwardly from a rear end of the sanitary napkin is bonded to an exterior surface of the release sheet at a position spaced rearwardly away from the pressure sensitive adhesive layers of the wing portions.

4 Claims, 9 Drawing Sheets

HYGIENE PRODUCT

BACKGROUND OF THE INVENTION

1. Field of the Invention

The present invention relates to a hygiene product having a folded sanitary napkin wrapped in a packaging sheet, more particularly, relates to a hygiene product having a release sheet covering garment surfaces of wing portions.

2. Description of the Related Art

Generally, sanitary napkins are individually packaged so as to keep them clean. The term "hygiene product" as used herein refers to such an individually packaged sanitary napkin. For example, a long sanitary napkin is wrapped in a packaging sheet formed of a resin film or the like, while being folded in three or four plies.

FIGS. 9A, 9B and 9C are perspective views showing a conventional hygiene product 10. This hygiene product 10 comprises an individually packaged sanitary napkin 1. The sanitary napkin 1 has an elongated main body portion and wing portions 2, 2 projecting from transversely opposed side edges of the main body portion. On garment surfaces of the wing portions 2, 2, there are provided pressure sensitive adhesive layers 3, 3, respectively. On a garment surface of the main body portion, on the other hand, there are provided pressure sensitive adhesive layers 4, 4.

This sanitary napkin 1 is packaged as follows. At first, the wing portions 2, 2 are folded back against a body surface of the main body portion, and then the pressure sensitive adhesive layers 3, 3 are covered with a release sheet 5. Thereafter, the sanitary napkin 1 and the release sheet 5 are laid on a packaging sheet 6 so that the pressure sensitive adhesive layers 4, 4 can adhere to a release-treated portion of the packaging sheet 6. The packaging sheet 6, the sanitary napkin 1 and the release sheet 5 thus stacked are first folded about a first fold axis 8a into a state of FIG. 9C. Then, they are folded about a second fold axis 8b into a state of FIG. 9B. At this time, an exterior surface of the release sheet 5 is adhered to an exterior surface of the packaging sheet 6 through an adhesive 7 applied to a front portion of the release sheet 5. Finally, they are folded about a third fold axis 8c into a state of FIG. 9A where only the packaging sheet 6 externally appears. Then, transversely opposed side portions of the packaging sheet 6 are sealed to provide sealed portions 9, 9 by heat embossing, and the front end of the packaging sheet 6 is secured by a lead tape 11.

This hygiene product 10 can be opened by peeling off the lead tape 11 and breaking the sealed portions 9, 9 to unfold the packaging sheet 6. At this time, since the packaging sheet 6 and the release sheet 5 are bonded to each other through the adhesive 7, the release sheet 5 is unfolded together with the packaging sheet 6, as shown in FIG. 10, so that the release sheet 5 is peeled from the pressure sensitive adhesive layers 3, 3 on the wing portions 2, 2. The packaging sheet 6 is further unfolded from the state of FIG. 10, and peeled from the pressure sensitive adhesive layers 4, 4 on the garment surface of the main body portion.

In the conventional hygiene product 10, the release sheet 5 separates from the sanitary napkin 1 at the time when the packaging sheet 6 is unfolded to the state of FIG. 10. That is, the pressure sensitive adhesive layers 3, 3 on the garment surfaces of the wing portions 2, 2 are exposed externally at an early stage of the opening procedure. Therefore, they may possibly adhere to the hand of a user or a garment at a subsequent stage of the opening procedure. In this case, the sanitary napkin 1 becomes difficult to wear. In addition, since an adhesive force of the pressure sensitive adhesive layers 3, 3 is decreased, the wing portions 2, 2 cannot certainly adhere to an outer side of a short panty when the sanitary napkin 1 is put on a crotch portion of the short panty.

In addition, since the body surface (liquid-receiving surface) of the main body portion of the sanitary napkin 1 is exposed externally at the beginning of the opening procedure, as shown in FIG. 10, there is a high probability that the hand of a user will contact the liquid receiving surface. Therefore, it is difficult to keep the sanitary napkin 1 clean.

SUMMARY OF THE INVENTION

The present invention has been worked out in view of the shortcoming in the prior art set forth above. It is therefore an object of the present invention to provide a hygiene product which can be opened without externally exposing pressure sensitive adhesive layers of wing portions and a body surface of a sanitary napkin at an early stage of an opening procedure, so that the sanitary napkin can be easily handled upon wearing and can be kept clean, as well as the sanitary napkin can be readily separated from a packaging sheet and a release sheet.

According to the present invention, there is provided a hygiene product comprising:

a sanitary napkin including an elongated main body portion having longitudinally opposed front and rear ends and wing portions protruding from transversely opposed side edges of the main body portion and folded back against a body surface of the main body portion;

a release sheet covering pressure sensitive adhesive layers provided on garment surfaces of the wing portions; and a packaging sheet having a release-treated portion covering a pressure sensitive adhesive layer provided on a garment surface of the main body portion, a stack of the packaging sheet, the sanitary napkin and the release sheet being so folded into the hygiene product that only the packaging sheet is exposed externally, wherein a rear protruding portion of the packaging sheet protruding rearwardly from the rear end of the sanitary napkin is folded back against an exterior surface of the release sheet which is not adhered to the pressure sensitive adhesive layers of the wing portions, and the rear protruding portion of the packaging sheet is bonded to the exterior surface of the release sheet at a position spaced rearwardly away from the pressure sensitive adhesive layers of the wing portions, wherein the stack is further folded at least once so that the front end of the sanitary napkin and a front edge of the packaging sheet adjacent to the front end of the sanitary napkin are laid on an exterior surface of the packaging sheet which is exposed externally.

In the hygiene product of the present invention, since the bond where the release sheet is fixed to the packaging sheet is positioned rearwardly away from the pressure sensitive adhesive layers of the wing portions, the release sheet can remain adhered to the pressure sensitive adhesive layers of the wing portions until a final stage of a procedure for opening the hygiene product. Therefore, the pressure sensitive adhesive layers of the wing portions can be prevented from being exposed externally at an early stage. In addition, most of the body surface of the main body portion can also be prevented from being exposed externally at an early stage. Since the release sheet and the packaging sheet are connected to each other through an adhesive, the packaging sheet can be separated together with the release sheet from the sanitary napkin when the packaging sheet is peeled from the garment surface of the main body portion, thereby facilitating the opening procedure.

Preferably, an interior surface of the packaging sheet having the release-treated portion thereon is bonded to the exterior surface of the release sheet.

In the case where the interior surface of the packaging sheet is bonded to the exterior surface of the release sheet, the bond can be easily provided at a position away from the pressure sensitive adhesive layers of the wing portions, as compared with the case where the exterior surface of the packaging sheet is bonded to the exterior surface of the release sheet. Therefore, an excessive peeling force hardly acts on the release sheet when the stack is unfolded during the opening procedure, so that the release sheet can be maintained for a relatively long time in a position covering the pressure sensitive adhesive layers of the wing portions.

In one embodiment, it is possible that the stack is folded about a first fold axis to form a first folded portion where the rear protruding portion is laid on the exterior surface of the release sheet and a bond where the rear protruding portion is bonded to the exterior surface of the release sheet, wherein
the stack is further folded about a second fold axis positioned between the bond and the rear end of the sanitary napkin to form a second folded portion where the first folded portion is laid on the body surface of the main body portion of the sanitary napkin, wherein
the front end of the sanitary napkin and the front edge of the packaging sheet is laid on the second folded portion and transversely opposed side portions of the packaging sheet are sealed.

If the stack is thus folded, the hygiene product can be made compact for the carrying convenience.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
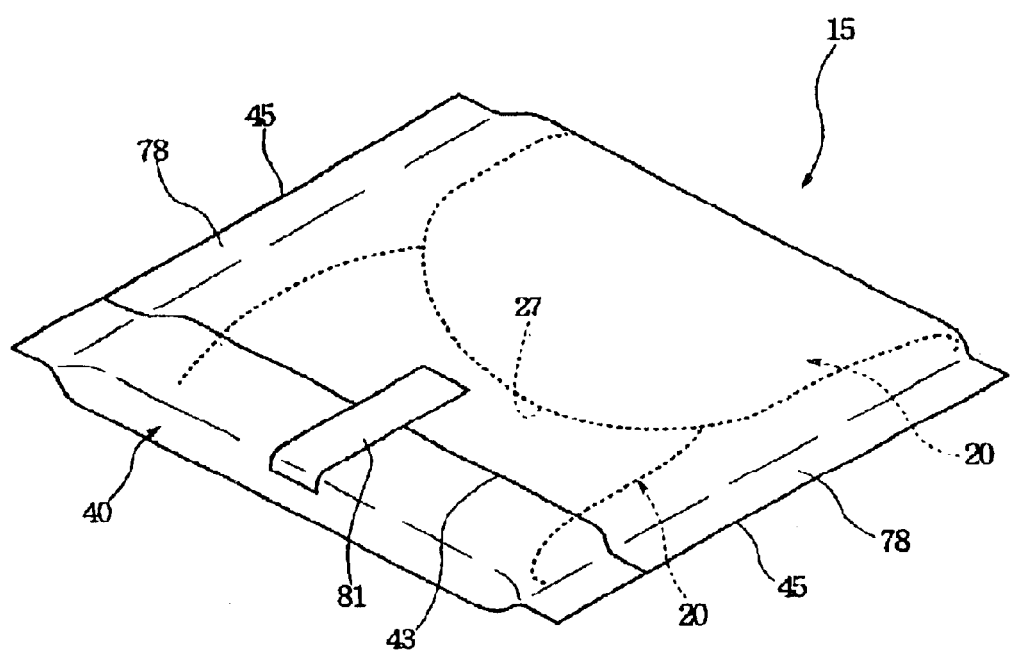
FIG. 1 is a perspective view showing a hygiene product according to one embodiment of the present invention in an unopened state.
Figure 2:
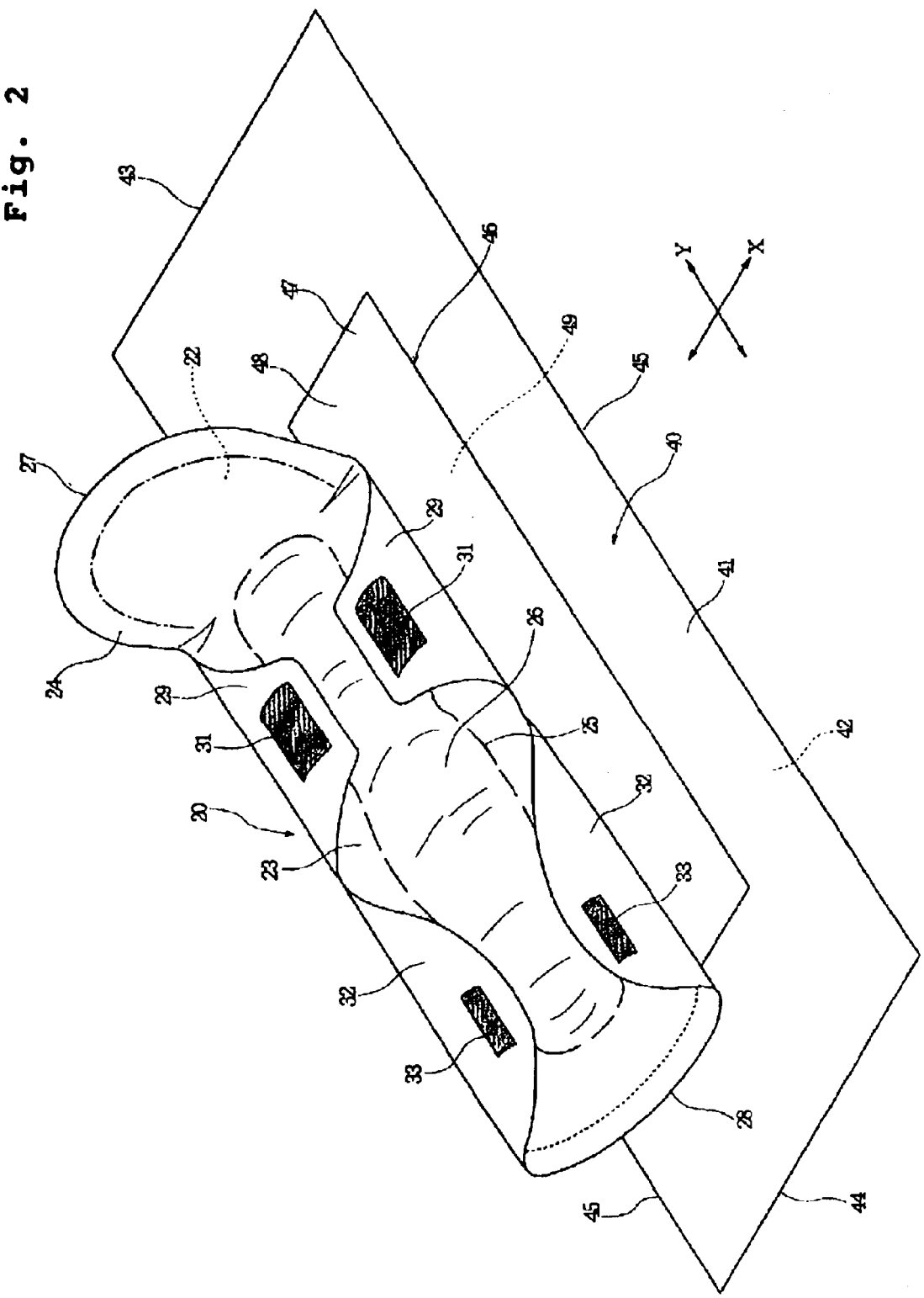
FIG. 2 is a perspective view showing a sanitary napkin and a packaging sheet.
Figure 3:
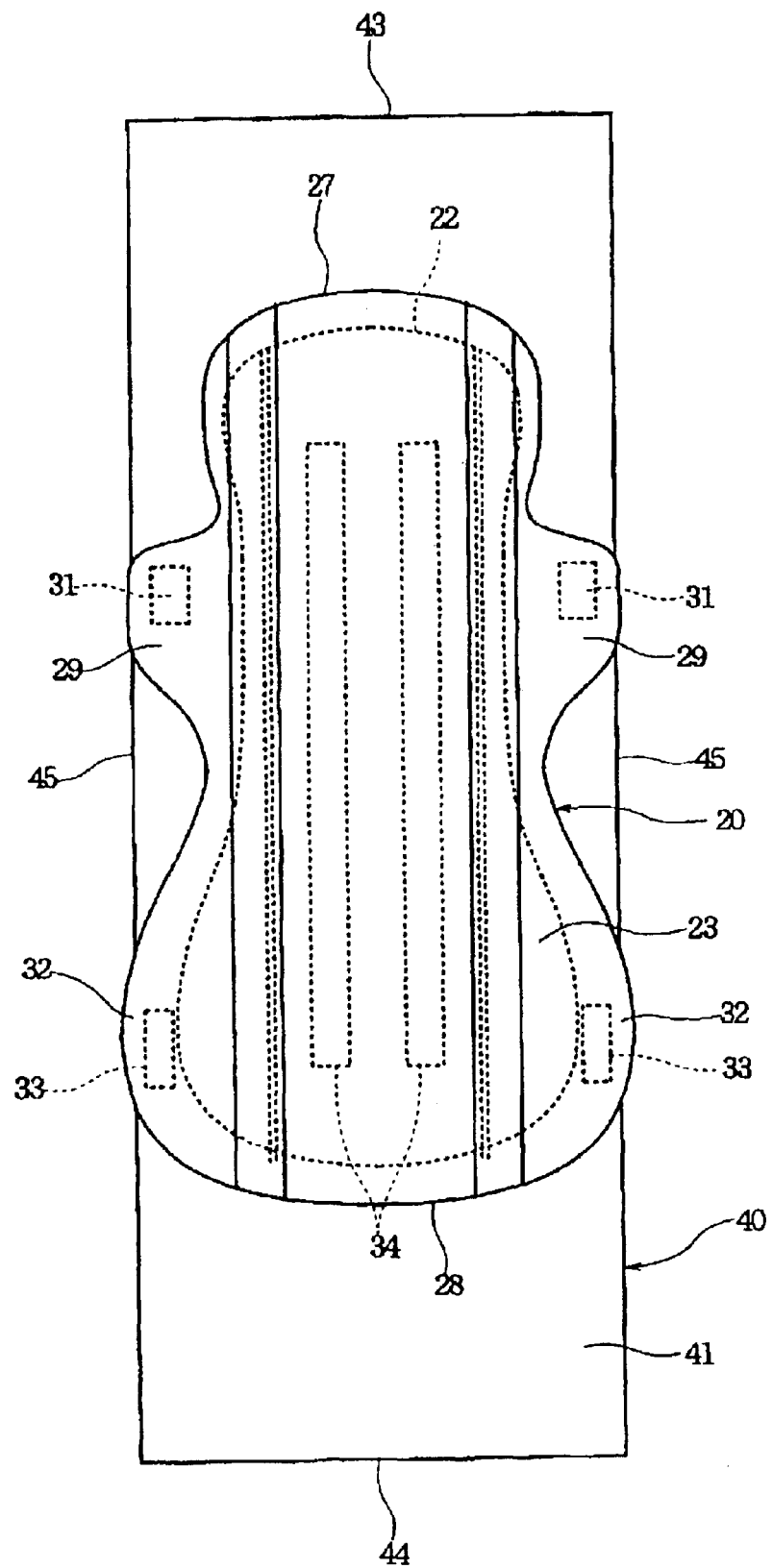
FIG. 3 is a top plan view showing a state where the sanitary napkin is put on the packaging sheet.
Figure 4:
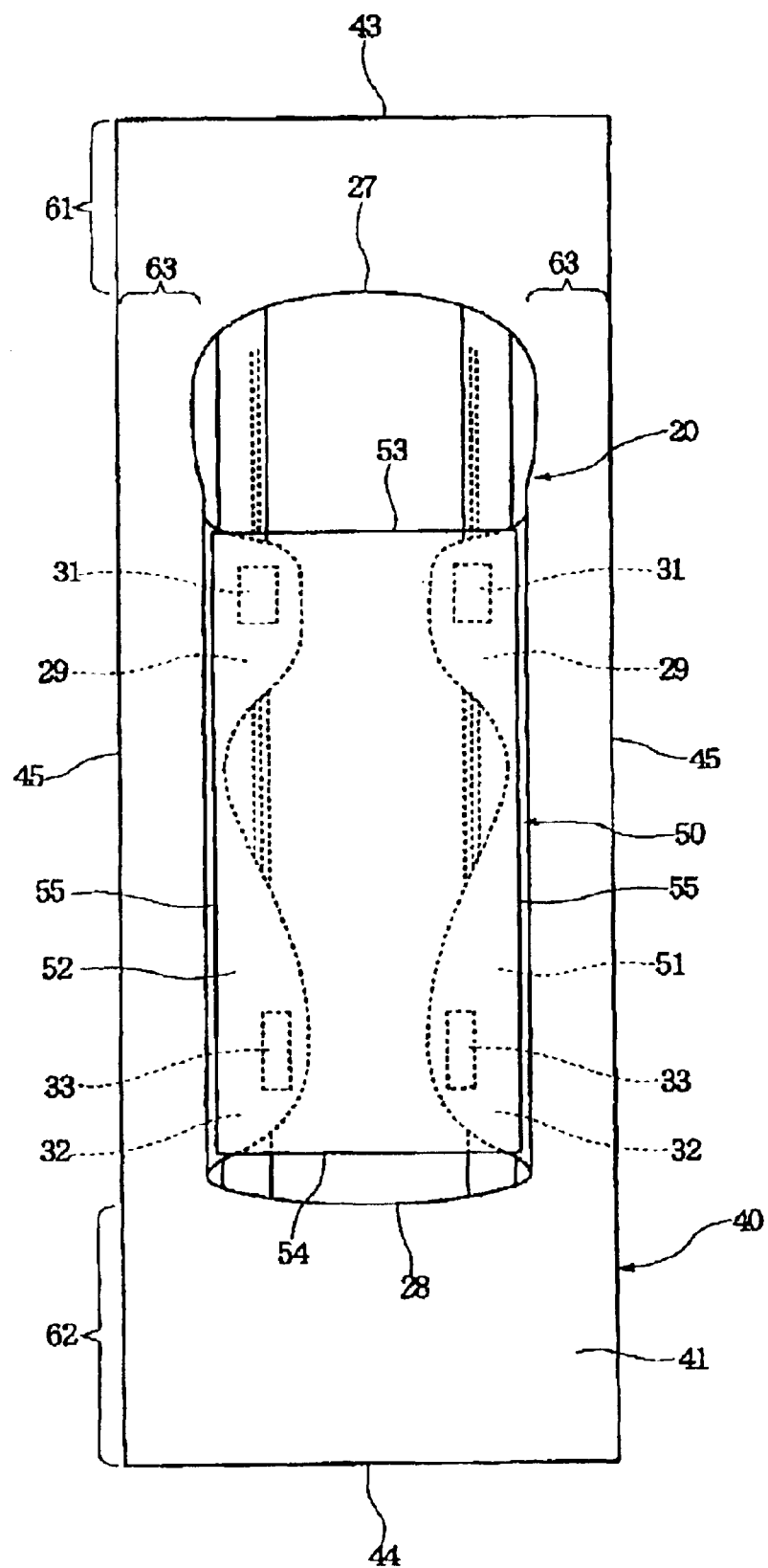
FIG. 4 is a top plan view showing a state where a release sheet is put on the sanitary napkin.
Figure 7:
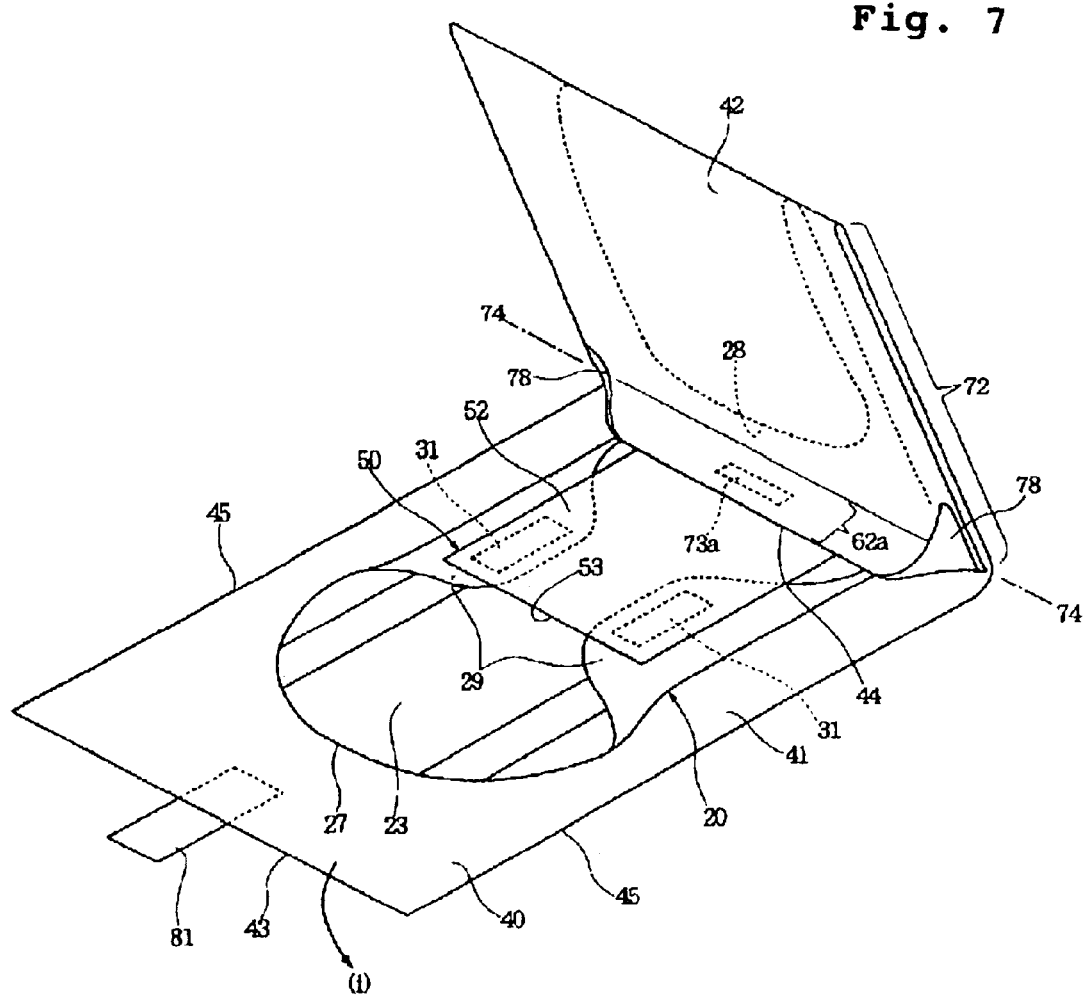
FIG. 7 is a perspective view explaining a procedure for opening the hygiene product.
Figure 8:
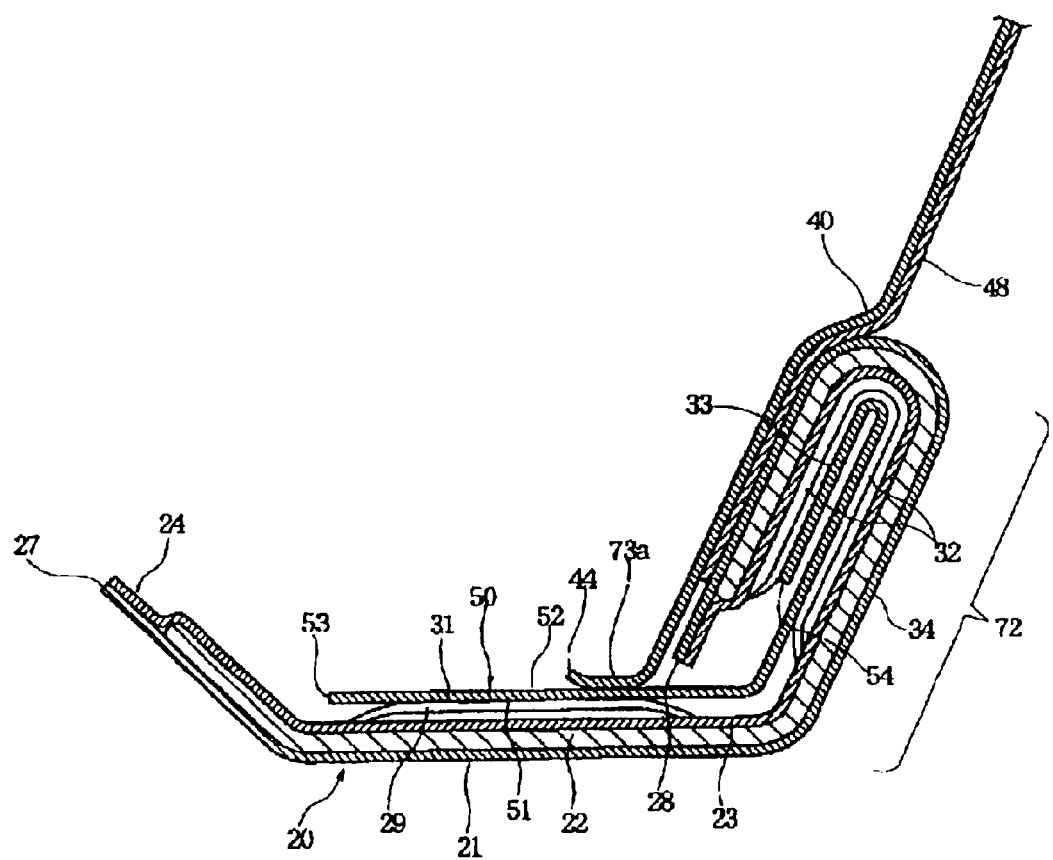
FIG. 8 is a sectional view showing a state where the opening is advanced more than the state of FIG. 7.
Figure 9A:
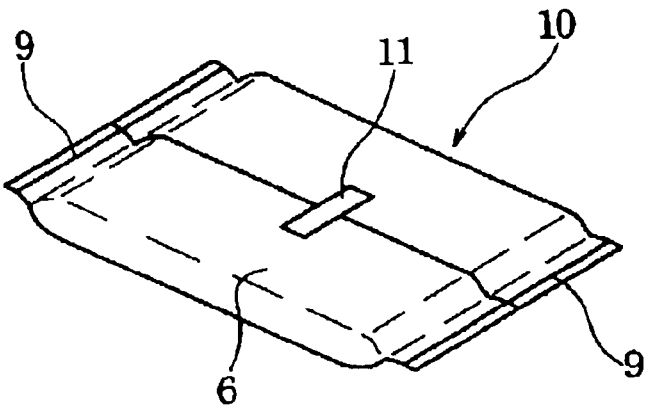
FIGS. 9A, 9B and 9C are perspective views explaining a folding procedure for a conventional hygiene product.
Figure 9B:
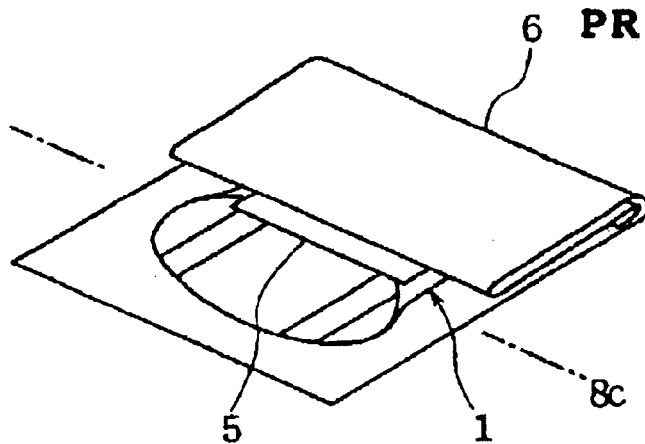
Figure 9C:
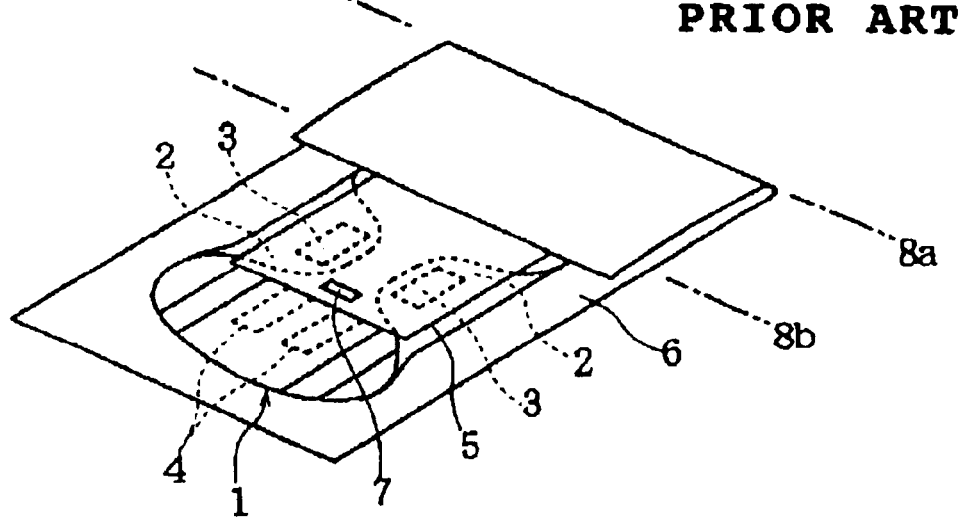
Figure 10:
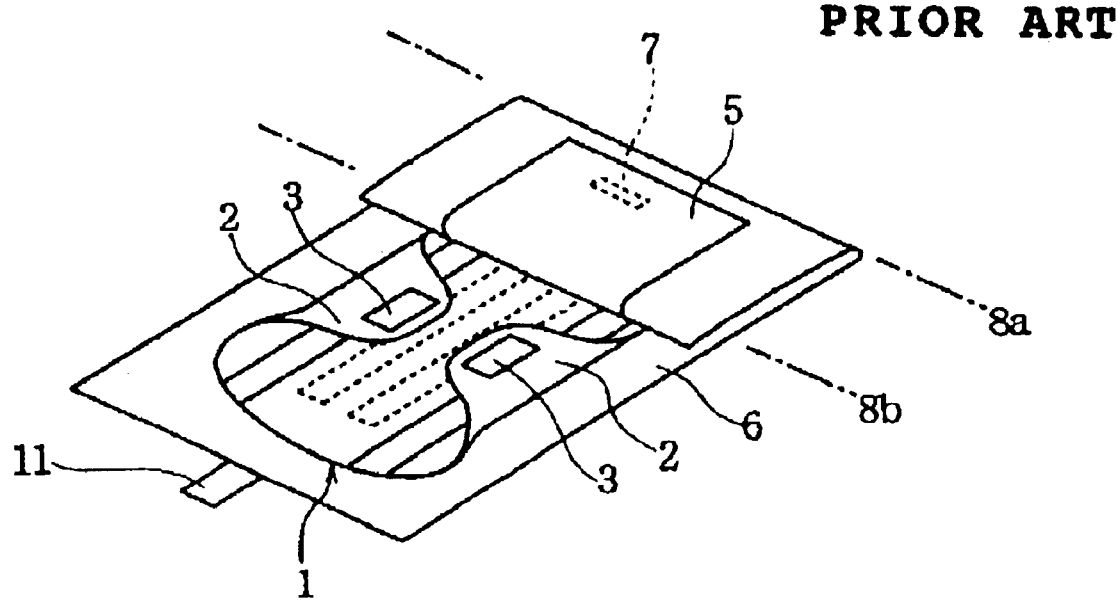
FIG. 10 is a sectional view showing the conventional hygiene product in the middle of an opening procedure.

FIG. 1 is a perspective view showing a hygiene product 15 according to one embodiment of the present invention in an unopened state; FIG. 2 is a perspective view showing a sanitary napkin 20 and a packaging sheet 40; FIG. 3 is a top plan view showing a state where the sanitary napkin 20 is put on the packaging sheet 40; FIG. 4 is a top plan view showing a state where a release sheet 50 is put on the sanitary napkin 20; FIGS. 5A, 5B and 5C and FIGS. 6A and 6B are perspective views explaining a folding procedure; FIG. 7 is a perspective view explaining an opening procedure; and FIG. 8 is a sectional view showing a state where the opening is advanced more than the state of FIG. 7. It should be noted that the sanitary napkin 20 has a body surface and a garment surface. As used herein, "body surface" means that surface of the napkin which is intended to be worn toward or adjacent to the body of a wearer, while the "garment surface" is on the opposite side and is intended to be worn toward or placed adjacent to an undergarment when the napkin is worn.

The hygiene product 15 of FIG. 1 is an individually packaged sanitary napkin, wherein the sanitary napkin 20 is folded together with the packaging sheet 40 and the release sheet 50 so that the packaging sheet 40 appears externally.

The sanitary napkin 20 has an elongated main body portion, and wing portions 29, 29 and rear flap portions 32, 32 protruding from transversely opposed side edges of the main body portion. It should be noted that the wing portions 29, 29 and the rear flap portions 32, 32 refer to the portions to be folded back against the body surface of the main body portion before the release sheet 50 is put on the sanitary napkin 20, as shown in FIG. 4. The sanitary napkin 20 is constructed to include: a liquid impermeable backsheet 21; a liquid absorbent layer (absorbent core) 22 disposed on the backsheet 21; and a liquid permeable topsheet 23 covering the liquid absorbent layer 22, as shown in the sectional view of FIG. 8. The liquid absorbent layer 22 is of an elliptical or hour-glass shape. In a peripheral region 24 outside the liquid absorbent layer 22, the backsheet 21 and the topsheet 23 are bonded to each other through a hot-melt type adhesive or the like.

As shown in FIG. 2, the sanitary napkin 20 is formed with a compressed groove 25, where the topsheet 23 and the liquid absorbent layer 22 are heated under pressure by heat embossing. In a portion 26 surrounded by the compressed groove 25, the body surface of the sanitary napkin 20 is raised (hereinafter referred to as raised portion 26). The raised portion 26 is intended to come into close contact with the genital organ when the sanitary napkin 20 is worn on the crotch of a woman.

The sanitary napkin 20 has a front end 27 and a rear end 28. In FIG. 2, the front end 27 is oriented to the right-hand side of the drawing. In FIGS. 3 and 4, the front end 27 is oriented to the top of the drawing. In FIGS. 5A, 5B, 5C, 6A, 6B, 7 and 8, the front end 27 is oriented to the left-hand side of the drawing.

As shown in FIGS. 2 and 3, the wing portions 29, 29 are positioned closer to the front end 27 than the rear flap portions 32, 32. The wing portions 29, 29 are provided on their garment surfaces with first pressure sensitive adhesive layers 31, 31. The rear flap portions 32, 32 are provided on their garment surfaces with second pressure sensitive adhesive layers 33, 33. On the garment surface of the main body portion, moreover, third pressure sensitive adhesive layers 34, 34 are provided in the form of two strips extending in a longitudinal direction of the sanitary napkin 20, as shown in FIG. 3.

This sanitary napkin 20 is intended for nighttime use. Upon use, the main body portion of the sanitary napkin 20 is adhered to an inner side of a crotch portion of a short panty through the third pressure sensitive adhesive layers 34, 34, and the rear flap portions 32, 32 in an unfolded state are adhered to an inner side of the short panty through the second pressure sensitive adhesive layers 33, 33. Then, the wing portions 29, 29 are folded around side edges of the crotch portion of the short panty and adhered to an outer side of the crotch portion of the short panty through the first pressure sensitive adhesive layers 31, 31. The sanitary napkin 20 thus mounted can be prevented from being displaced from the crotch portion of the short panty. In addition, since the rear portion of the sanitary napkin 20 including the rear flap portions 32, 32 can cover a large area of a lower portion of the buttocks, rearward leakage of menstrual blood can be effectively prevented.

The backsheet 21 may be formed of a resin film made of polymeric material such as polyethylene (PE), polypropylene (PP) or ethylene-vinyl acetate copolymer (EVA). Preferably used is a moisture permeable (breathable) film that is formed by adding filler to the polymeric material and stretching it to have fine apertures.

The liquid absorbent layer 22 may be formed of a mixture of comminuted pulp and superabsorbent polymer, superabsorbent polymer wrapped in a cellulose sheet, cellulose fibers in the form of a sheet, or the like.

The topsheet 23 may be formed of a nonwoven fabric comprising synthetic fibers treated to be hydrophilic, a synthetic resin film formed with a large number of liquid passage holes, or the like.

The individual pressure sensitive adhesive layers 31, 33 and 34 may be formed of a hot-melt type pressure sensitive adhesive.

The packaging sheet 40 is heat-fusible, and may be formed of a film comprising thermoplastic resin such as polyethylene (PE), or a spunbonded nonwoven fabric comprising thermoplastic synthetic fibers such as polypropylene (PP) or polyester (PET). In an alternative, the packaging sheet 40 may be formed of a spunbond-meltblown-spunbond (S-M-S) laminate in which a meltblown nonwoven fabric comprising thermoplastic resin fibers such as PP or PET is sandwiched between two spunbonded nonwoven fabrics comprising thermoplastic resin fibers such as PP or PET.

The packaging sheet 40 is of a rectangular shape having a front edge 43, a rear edge 44 and left and right side edges 45, 45. The packaging sheet 40 has an interior surface 41 which is intended to come into contact with the sanitary napkin 20 when the sanitary napkin 20 is put on the packaging sheet 40, and an exterior surface 42 which is on the opposite side and intended to appear externally in the state of FIG. 1.

As shown in FIG. 2, the interior surface 41 of the packaging sheet 40 has a release-treated portion 46 at the center thereof. In the embodiment shown, the release-treated portion 46 is formed by bonding a release sheet 47 to the center of the interior surface 41 of the packaging sheet 40. The release sheet 47 may be formed by applying a release agent such as silicone resin to the top surface 48 of a substrate such as paper, resin sheet or laminate of paper and resin layer. The bottom surface 49 of the substrate is not treated with a release agent, and fixed on the interior surface 41 of the packaging sheet 40 through an adhesive. However, such a release-treated portion may be formed in any manner as long as the third pressure sensitive adhesive layers 34 can be readily peeled from the interior surface 41 of the packaging sheet 40. For example, in the case where the packaging sheet 40 is formed of a resin sheet, the release agent may be directly applied to at least a central portion of the interior surface 41 of the packaging sheet 40. In the case where the packaging sheet 40 is formed of a laminate of paper and resin layer and the resin layer of the laminate appears on the interior surface 41 of the packaging sheet 40, on the other hand, the release agent may be directly applied to the surface of the resin layer.

The release sheet 50, which is to be put on the sanitary napkin 20 after the wing portions 29, 29 and the rear flap portions 32, 32 are folded back against the body surface of the main body portion, is similar to the release sheet 47. The release sheet 50 has an interior surface 51 which is intended to come into contact with the wing portions 29, 29 and the rear flap portions 32, 32, and an exterior surface 52 which is on the opposite side and appears in FIG. 4. The interior surface 51 is treated with a release agent; and the exterior surface 52 is not treated with any release agent. The release sheet 50 is of an elongated rectangular shape having a front edge 53, a rear edge 54 and left and right side edges 55, 55.

Next, a procedure for folding the packaging sheet 40, the sanitary napkin 20 and the release sheet 50 into the hygiene product 15 will be described.

At first, the sanitary napkin 20 is put on the interior surface 41 of the packaging sheet 40, as shown in FIG. 4. Here, the third pressure sensitive adhesive layers 34, 34 on the garment surface of the main body portion of the sanitary napkin 20 are adhered to the top surface 48 of the release sheet 47 bonded to the interior surface 41 of the packaging sheet 40, and the wing portions 29, 29 and the rear flap portions 32, 32 are folded back against the body surface of the main body portion of the sanitary napkin 20. The first pressure sensitive adhesive layers 31, 31 of the wing portions 29, 29 and the second pressure sensitive adhesive layers 33, 33 of the rear flap portion 32, 32 are adhered to the interior surface (or release-treated surface) 51 of the release sheet 50. In the embodiment shown, the release sheet 50 is provided such that none of the front edge 53, the rear edge 54 and the left and right side edges 55, 55 protrude from the sanitary napkin 20.

In the state of FIG. 4, the packaging sheet 40 has a front protruding portion 61, a rear protruding portion 62 and side protruding portions 63, 63 that do not overlap with the sanitary napkin 20. More specifically: the front protruding portion 61 refers to the portion protruding forwardly from the front end 27 of the sanitary napkin 20 to the front edge 43 by a predetermined length; the rear protruding portion 62 refers to the portion protruding rearwardly from the rear end 28 of the sanitary napkin 20 to the rear edge 44 by a predetermined length; and the side protruding portions 63, 63 refer to portions slightly protruding sideways from the side edges of the main body portion of the sanitary napkin 20 to the side edges 45, 45.

After the packaging sheet 40, the sanitary napkin 20 and the release sheet 50 are stacked as shown in FIG. 4, the stack is folded.

Figure 5A:
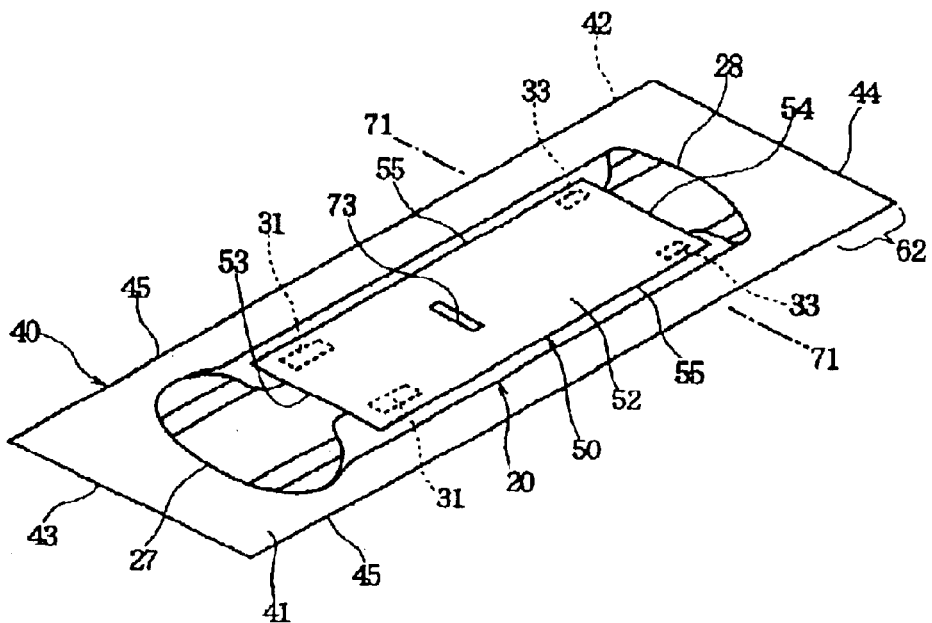
FIGS. 5A, 5B and 5C are perspective views sequentially explaining a procedure for folding a stack of the packaging sheet, the sanitary napkin and the release sheet.
Figure 5B:
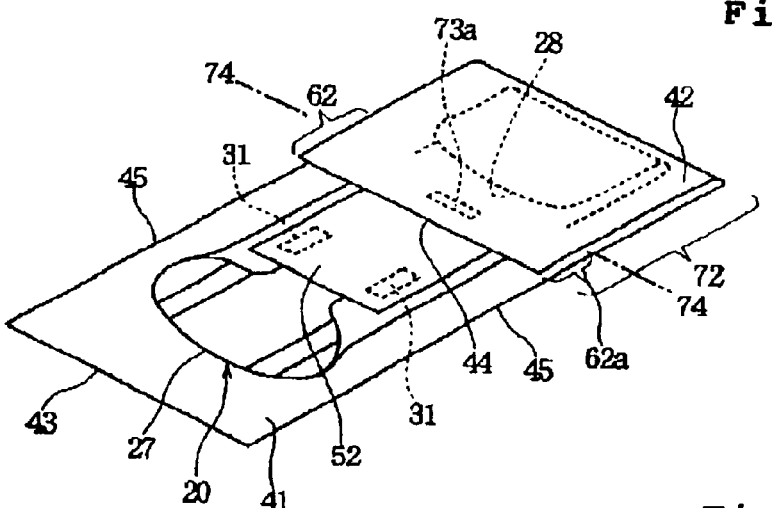

FIG. 5A shows a first fold axis 71 transversely crossing the rear portion of the sanitary napkin 20, slightly ahead of the second pressure sensitive adhesive layers 33, 33. In addition, FIG. 5A shows an adhesive 73 such as hot-melt that is applied to the exterior surface 52 of the release sheet 50, behind the first pressure sensitive adhesive layers 31, 31. The stack is first folded about the first fold axis 71, so that a portion of the stack behind the first fold axis 71 is laid on the remaining portion of the stack, as shown in FIG. 5B. This overlapping portion is referred to as first folded portion 72. Upon formation of the first folded portion 72, the interior surface 41 of the packaging sheet 40 in the rear protruding portion 62 is bonded and fixed to the exterior surface 52 of the release sheet 50 through the adhesive 73, thereby forming a bond 73a. Since the interior surface 41 of the packaging sheet 40 is bonded to the exterior surface 52 of the release sheet 50, the bond 73a can be positioned sufficiently away from the first pressure sensitive adhesive layers 31, 31, as compared with the case where the exterior surface 42 of the packaging sheet 40 is bonded to the exterior surface 52 of the release sheet 50.

Figure 5C:
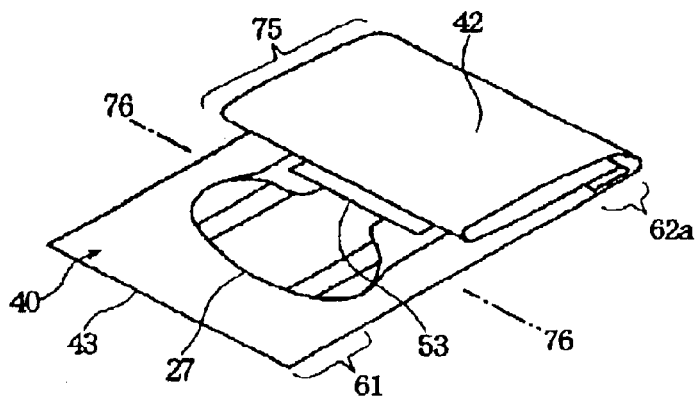

The stack is then folded about a second fold axis 74 that is positioned between the bond 73a and the rear end 28 of the sanitary napkin 20 in the folded configuration of FIG. 5B, so that a portion of the first folded portion 72 behind the second fold axis 74 is laid on the remaining portion of the stack, as shown in FIG. 5C. This overlapping portion is referred to as second folded portion 75. Here, an end portion of the rear protruding portion 62 of the packaging sheet 40 is referred to as folded portion 62a.

Figure 6A:
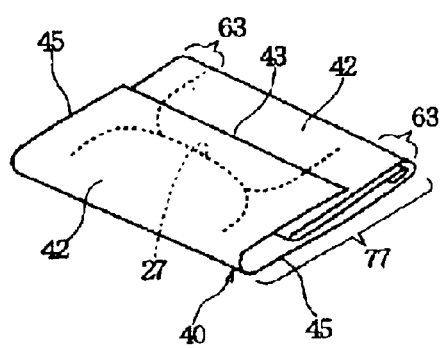
FIGS. 6A and 6B are perspective views sequentially explaining the folding procedure.

Finally, the stack is folded about a third fold axis 76 that is positioned ahead of the first pressure sensitive adhesive layers 31, 31 and the front edge 53 of the release sheet 50, so that the front end 27 of the sanitary napkin 20 and the front edge 43 of the packaging sheet 40 are laid on the second folded portion 75 to come into contact with the exterior surface 42 of the packaging sheet 40, as shown in FIG. 6A. Thus, there is obtained a folded structure 77 of FIG. 6A, in which the sanitary napkin 20 folded about three fold axes is covered with the packaging sheet 40.

Figure 6B:
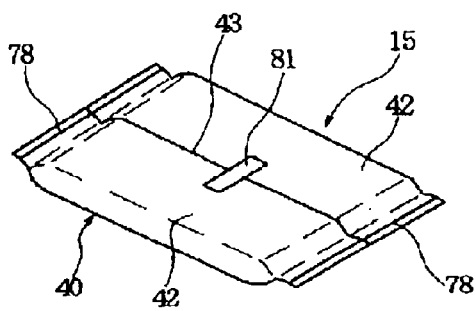

In this folded structure 77, each side protruding portion 63 of the packaging sheet 40, that is folded back upon itself without overlapping the sanitary napkin 20, is welded and sealed by heat embossing or the like, thereby forming side sealed portions 78, 78, as shown in FIG. 6B. Therefore, the sanitary napkin 20 is sealed in the packaging sheet 40. In addition, a lead tape 81 is adhered on the exterior surface 42 of the packaging sheet to cross the front edge 43. Thus, the hygiene product 15 is completed.

In the hygiene product 15, as shown in FIG. 5B, the interior surface 41 of the packaging sheet 40 is bonded to the exterior surface 52 of the release sheet 50 through the adhesive 73, thereby forming the bond 73a that is positioned behind the first pressure sensitive adhesive layers 31, 31 and in the vicinity of the second fold axis 74. More specifically, the bond 73a is positioned between the second fold axis 74 and the third fold axis 76 and closer to the second fold axis 74 than to the center between the second fold axis 74 and the third fold axis 76.

For the convenience's sake, the packaging sheet 40 has been described as a sheet cut into a size suitable for the final product in advance of the folding procedure. In an actual production process, however, it is preferred that a band-shaped packaging sheet having a width equal to the length of the packaging sheet 40 is continuously fed in the X-direction. In this case, a plurality of sanitary napkins 20 (each combined with the release sheet 50) can be provided on the band-shaped packaging sheet at spaced intervals in the X-direction and sequentially folded together with the band-shaped packaging sheet. After completion of the folding procedure, then, the band-shaped packaging sheet is sealed between adjacent sanitary napkins to provide the side sealed portions 78, and cut along the side sealed portions 78 into individual hygiene products 15.

Next, an optimal procedure for opening the hygiene product 15 of FIGS. 1 and 6B will be described.

At first, the lead tape 81 is peeled off and the front edge 43 of the packaging sheet 40 is removed away from the second folded portion 75 while breaking the seal of the packaging sheet 40 at the side sealed portions 78, 78. FIG. 7 shows a state where after unfolded about the third fold axis 76, the stack is further unfolded about the second fold axis 74.

As has been described hereinabove, the bond 73a where the packaging sheet 40 and the release sheet 50 are bonded and fixed to each other is positioned behind the first pressure sensitive adhesive layers 31, 31 and in the vicinity of the second fold axis 74. Therefore, the release sheet 50 remains adhered to the first pressure sensitive adhesive layers 31, 31 at the time when the stack is unfolded to the state of FIG. 7. That is, since the bond 73a can be provided sufficiently away from the first pressure sensitive adhesive layers 31, 31, as compared with the case where the exterior surface 42 of the packaging sheet 40 is bonded to the exterior surface 52 of the release sheet 50, the state where the first pressure sensitive adhesive layers 31, 31 are covered with the release sheet 50 can be maintained longer.

Especially since the packaging sheet 40 has the folded portion 62a folded about the second fold axis 74 and the interior surface 41 of the packaging sheet 40 is bonded in the folded portion 62a to the exterior surface 52 of the release sheet 50, a large peeling force does not act on the release sheet 50 even when the stack is unfolded to the state of FIG. 7, so that the folded portion 62a can be kept in contact with the exterior surface 52 of the release sheet 50.

In the state of FIG. 7, since the first pressure sensitive adhesive layers 31, 31 remain covered with the release sheet 50, the first pressure sensitive adhesive layers 31, 31 can be prevented from unexpectedly adhering to the hand of a user or a garment. In addition, since most of the topsheet 23 also remains covered with the release sheet 50 so as not to contact the fingers of a user, the body surface of the main body portion of the sanitary napkin 20 can be kept clean.

Subsequently, the sanitary napkin 20 can be separated from the packaging sheet 40 and the release sheet 50 as follows. In the state of FIG. 7, at first, the front end 27 of the sanitary napkin 20 is held by the fingers of one hand, and the front edge 43 of the packaging sheet 40 is held by the fingers of the other hand. Then, the packaging sheet 40 is peeled rearward (in a direction (i) of FIG. 7) from the garment surface of the main body portion of the sanitary napkin 20. At this time, the release sheet 47 on the interior surface 41 of the packaging sheet 40 can be peeled from the third pressure sensitive adhesive layers 34, 34 on the garment surface of the main body portion of the sanitary napkin 20.

FIG. 8 shows a state where the seal at the side sealed portions 78, 78 is completely broken and the packaging sheet 40 is peeled to a substantially flattened position. At this time, the packaging sheet 40 still remains bonded and fixed to the exterior surface 52 of the release sheet 50 through the bond 73a. Therefore, when the packaging sheet 40 is further lifted up from the state of FIG. 8 while holding the front end 27 of the sanitary napkin 20, the packaging sheet 40 can be completely peeled from the third pressure sensitive adhesive layers 34, 34, as well as the release sheet 50 connected to the packaging sheet 40 through the bond 73a can be peeled from the first pressure sensitive adhesive layers 31, 31 and the second pressure sensitive adhesive layers 33, 33. As a result, the sanitary napkin 20 can be separated from the packaging sheet 40 and the release sheet 50.

As has been described hereinabove, the sanitary napkin 20 can easily be separated from the packaging sheet 40 and the release sheet 50 that remain connected to each other. In addition, the first pressure sensitive adhesive layers 31, 31, the second pressure sensitive adhesive layers 33, 33 and most of the topsheet 23 can be prevented from being exposed externally until the final stage of the opening procedure, as shown in FIG. 8.

In the foregoing embodiment, the stack is folded three times about the first fold axis 71, the second fold axis 74 and the third fold axis 76. However, the hygiene product may be obtained by folding the stack only twice. In this case, for example, the front end 27 of the sanitary napkin 20 and the front edge 43 of the packaging sheet 40 may be laid on the upper side of the first folded portion 72 from the state of FIG. 5B.

As has been described hereinabove, since the hygiene product of the present invention can be opened without exposing the pressure sensitive adhesive layers of the wing portions at the first stage of the opening procedure, the pressure sensitive adhesive layers can be prevented from unexpectedly adhering to the hand of a user or a garment. In addition, since the body surface of the main body portion of the sanitary napkin remains covered with release sheet, it can be kept clean. Moreover, since the packaging sheet and the release sheet are connected to each other, the packaging sheet and the release sheet can be integrally separated from the sanitary napkin, thereby facilitating the opening procedure.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A hygiene product comprising:
    a sanitary napkin including an elongated main body portion having longitudinally opposed front and rear ends and wing portions protruding from transversely opposed side edges of the main body portion and folded back against a body surface of the main body portion;
    a release sheet covering pressure sensitive adhesive layers provided on garment surfaces of the wing portions, the release sheet having an interior surface in contact with the pressure sensitive adhesive layers of the wing portions and an exterior surface opposite from the interior surface; and
    a packaging sheet having an interior surface with a release-treated portion covering a pressure sensitive adhesive layer provided on a garment surface of the main body portion and an exterior surface opposite from the interior surface, a stack of the packaging sheet, the sanitary napkin and the release sheet being so folded twice or more to form the hygiene product in which only the packaging sheet is exposed externally, wherein
    the stack is first folded such that a rear protruding portion of the packaging sheet which protrudes rearwardly from the rear end of the sanitary napkin before folding is laid on the exterior surface of the release sheet, and the rear protruding portion being bonded to the exterior surface of the release sheet at a position located rearwardly away from the pressure sensitive adhesive layers of the wing portions and forwardly away from the rear end of the sanitary napkin before folding, the stack is then folded at least once such that the front end of the sanitary napkin and a front edge of the packaging sheet adjacent to the front end of the sanitary napkin are laid on an exterior surface of the packaging sheet which is exposed externally.

2. A hygiene product as set forth in claim 1, wherein the an interior surface of the packaging sheet having the release-treated portion thereon is bonded to the exterior surface of the release sheet.

3. A hygiene product as set forth in claim 1, wherein the stack is first folded about a first fold axis to form a first folded portion where the rear protruding portion is laid on the exterior surface of the release sheet and a bond where the rear protruding portion is bonded to the exterior surface of the release sheet,
    the stack is folded about a second fold axis positioned between the bond and the rear end of the sanitary napkin to form a second folded portion where the first folded portion is laid on the body surface of the main body portion of the sanitary napkin, and
    the stack is further folded such that the front end of the sanitary napkin and the front edge of the packaging sheet is laid on the second folded portion and transversely opposed side portions of the packaging sheet are sealed.

4. A hygiene product as set forth in claim 1, wherein the sanitary napkin further includes rear flap portions rearward of the wing portions, the rear flap portions protruding from the transversely opposed side edges of the main body portion and folded back against the body surface of the main body portion, wherein
    pressure sensitive adhesive layers provided on garment surfaces of the rear flap portions are also in contact with the interior surface of the release sheet, and the rear protruding portion is bonded to the exterior surface of the release sheet at a position located forwardly away from the pressure sensitive adhesive layers of the rear flap portions before folding.

* * * * *